US005749828A

United States Patent [19]
Solomon et al.

[11] Patent Number: 5,749,828
[45] Date of Patent: May 12, 1998

[54] BENDING NECK FOR USE WITH INVASIVE MEDICAL DEVICES

[75] Inventors: Rodney J. Solomon, Andover; Hubert K. Yeung, Lynnfield, both of Mass.

[73] Assignee: Hewlett-Packard Company, Palo Alto, Calif.

[21] Appl. No.: 576,940

[22] Filed: Dec. 22, 1995

[51] Int. Cl.$^6$ .................................................. A61B 1/00
[52] U.S. Cl. ......................... 600/141; 600/142; 600/146; 600/139
[58] Field of Search .................................. 600/146, 147, 600/148, 149, 150, 151, 152, 139, 140, 141, 142, 143, 144; 138/120, 118, 118.1

[56] References Cited

U.S. PATENT DOCUMENTS 5,251,611  10/1993  Zehel et al. ............................. 600/141

Primary Examiner—Beverly M. Flanagan
Attorney, Agent, or Firm—John L. Imperato

[57] ABSTRACT

In the present invention, an easily assembled, reliable bending neck is formed for use with invasive medical devices. The bending neck comprises a series of pivotally hinged segments, each having a central lumen. The segments are positioned end-to-end, while the lumens collectively provide a shaft to accommodate delicate interconnections to a head assembly attached to the bending neck. Separate from the lumen are channels formed in each segment. The channels, combined from each segment, run the length of the bending neck and are aligned to accommodate cables used to articulate the bending neck. The separation of the lumen from the channels isolates the delicate interconnections from the motion of the cables as the bending neck is articulated.

The cables and the separated lumen and channels form a bending neck having high reliability, that is easy to assemble, for use with invasive medical devices. In a one embodiment of the present invention, a bending neck has a pair of cables and its articulation is limited to lateral directions. In an alternate embodiment, the bending neck has three cables and is articulable in combinations of the lateral and vertical directions. The present invention includes an assembly method for the bending neck.

4 Claims, 8 Drawing Sheets

BENDING NECK FOR USE WITH INVASIVE MEDICAL DEVICES

FIELD OF THE INVENTION

This invention relates generally to medical devices inserted into a patient's body and particularly to a bending neck used with these invasive medical devices.

BACKGROUND OF THE INVENTION

Endoscopes, orthoscopes, ultrasound transducer probes and other invasive, imaging and therapeutic, medical devices are inserted into a patient's body. For example, transesophageal ultrasound transducer probes are inserted down a patient's esophagus to acquire ultrasound images of the patient's heart. Endoscopes containing optical fibers may be inserted orally or nasally to view the patient's lungs or digestive tract. Orthoscopes and other devices inserted into surgical incisions perform remotely controlled laser surgery. Although many types of medical devices are inserted into a patient's body, these invasive medical devices share some common attributes.

One attribute is that most of the invasive devices are articulated, or steered, remotely. For example, once a transesophageal ultrasound transducer probe is inserted down the esophagus, the tip of the probe is steered remotely so that an ultrasound beam may be accurately aimed at the heart. Another attribute is that these medical device have high reliability. Since use of these medical devices may be invasive to the patient, the patient may be treated with a topical anesthetic or may be otherwise prepared, for the insertion of the medical device into the body. If the device is unreliable, the patient preparation may need to be repeated, perhaps at a high cost or at discomfort to the patient.

One example of an invasive medical device used for imaging is the HP model number 21366A ultrasound transducer probe available from Hewlett-Packard Company. This type of probe incorporates a bending neck constructed from a series of rings each pivotally joined by a pair of aligned rivets. An ultrasound transducer is attached to the end of the bending neck and is located at the tip of the probe. Four pull cables are threaded through small holes formed in the aligned rivets inside the rings and the pull cables are retracted to articulate the bending neck. Interconnections to the ultrasound transducer are also routed through the center of the rings. As the pull cables are retracted to articulate the bending neck, there is a relative motion between the pull cables and the interconnections which may cause damage to the delicate interconnections. This type of bending neck is also labor intensive to assemble because the alignment of the small holes in the rivets is used to accommodate the pull cables. Once the small holes are precisely aligned, the pull cables are then meticulously threaded through the small holes of the rivets.

SUMMARY OF THE INVENTION

In the present invention, an easily assembled, reliable bending neck is formed for use with invasive medical devices. The bending neck comprises a series of pivotally hinged segments, each having a central lumen. The segments are positioned end-to-end, while the lumens collectively provide a shaft to accommodate delicate interconnections to a head assembly attached to the bending neck. Separate from the lumen are channels formed in each segment. The channels, combined from each segment, run the length of the bending neck and are aligned to accommodate cables used to articulate the bending neck. The separation of the lumen from the channels isolates the delicate interconnections from the motion of the cables as the bending neck is articulated.

The cables and the segments form a bending neck having high reliability, that is easy to assemble, for use with invasive medical devices. In a first embodiment of the present invention, a bending neck has a pair of cables and its articulation is limited to lateral directions. In an alternate embodiment, the bending neck has three cables and is articulable in combinations of the lateral and vertical directions. The present invention includes an assembly method for the bending neck.

DETAILED DESCRIPTION OF THE PREFERRED EMBODIMENT

Figure 1:
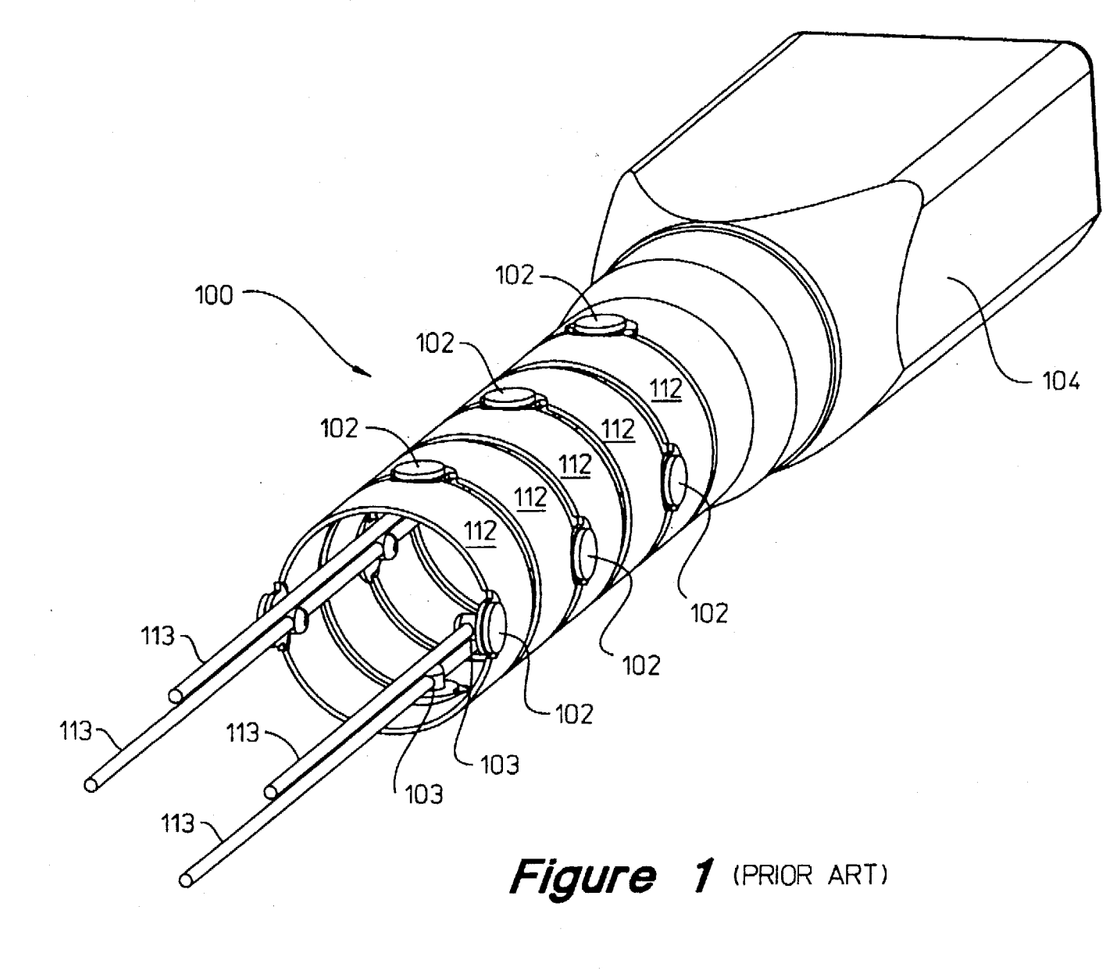
FIG. 1 shows a prior art bending neck.

FIG. 1 shows a prior art bending neck 100 and an attached head assembly 104. Four pull cables 113 are threaded through an aligned series of rivets 102 which each have a guide hole 103 oriented to accommodate one of the pull cables. The pull cables 113 run the length of the bending neck 100 and are each anchored at one end to the head assembly 104. The rivets 102 also provide pivot points between a series of rings 112 which are used to construct the bending neck 100. Electrical, fiber optic or other types of interconnections (not shown) are routed through the center of the rings 112 and run the length of the bending neck 100 and to the head assembly 104. Attached to the end of the bending neck 100, opposite the head assembly 104, is an insertion tube (not shown). The insertion tube is long and flexible to permit deep insertion of the bending neck 100 and head assembly 104, into the patient's body.

The bending neck 100 and attached head assembly 104 are inserted into the appropriate body cavity of the patient while the head assembly 104 is steered by articulation of the bending neck 100. The bending neck is articulated by retracting each of the pull cables 113. A steering wheel or other type of steering mechanism (not shown), attached to the pull cables 113 at the end of the insertion tube (opposite the end having the bending neck 100 attached) is used to retract the pull cables 113 in a controlled manner. This type of bending neck 100 is incorporated in the HP model number 21366A previously mentioned.

One feature of the prior art bending neck 100 is that the pull cables 113 and the interconnections are both located within the interior of the rings 112. Thus, as the pull cables 113 articulate the bending neck 100, there is a relative motion between the pull cables 113 and the interconnections. Over time, this relative motion may cause damage to the sensitive interconnections or may negatively affect the performance of the head assembly 104.

Figures 2A, 2B, 2C:
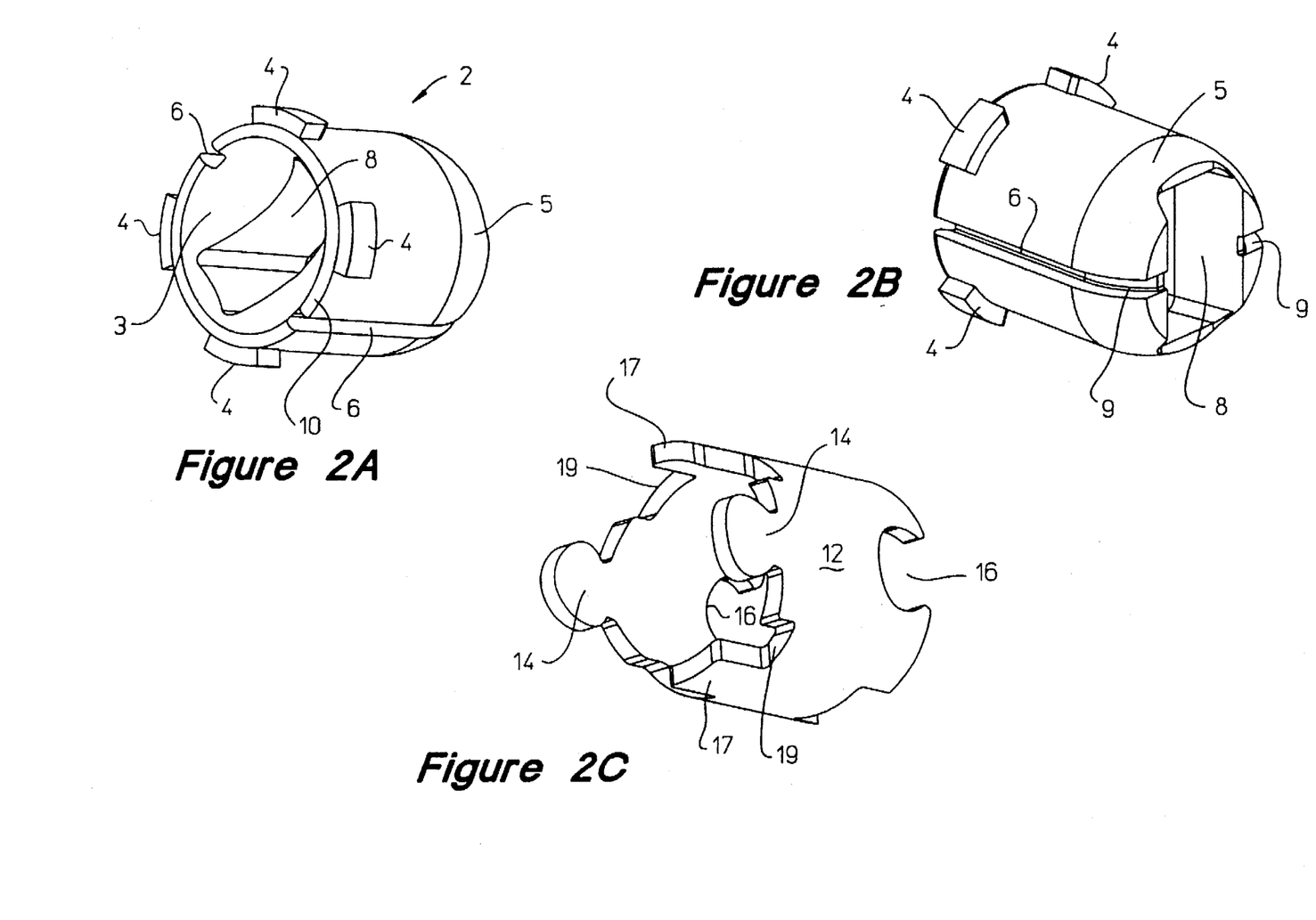
FIGS. 2A, 2B and 2C show perspective views of a link and a sleeve used to construct a bending neck of the present invention.

FIG. 2A is a first perspective view of a link 2 used to construct a bending neck of the present invention. At one end, the link 2 has a socket 3. Two diametrically opposed channels 6 run lengthwise along the link's outer surface and a lumen 8, provides a center opening through the length of the link 2. One or more tabs 4 is dispersed along a rim 10 of the socket 3.

FIG. 2B is a second perspective view of the link 2, showing a ball 5 formed at the end of the link 2 that is opposite from the socket 3. A curved portion 9 of each of the diametrically opposed channels 6 follows the curvature of the ball 5.

FIG. 2C shows a sleeve 12 also used to construct the bending neck of the present invention. The sleeve 12 has a pair of diametrically opposed swivel joints 14 at one end and a pair of diametrically opposed swivel sockets 16. A pair of diametrically opposed finger joints 17 are formed at the end of the sleeve 12, rotationally offset from the swivel joints 14 by 90°. On the other end of the sleeve 12, a pair of finger sockets 19 are rotationally aligned with the finger joints 17.

Figures 3A, 3B:
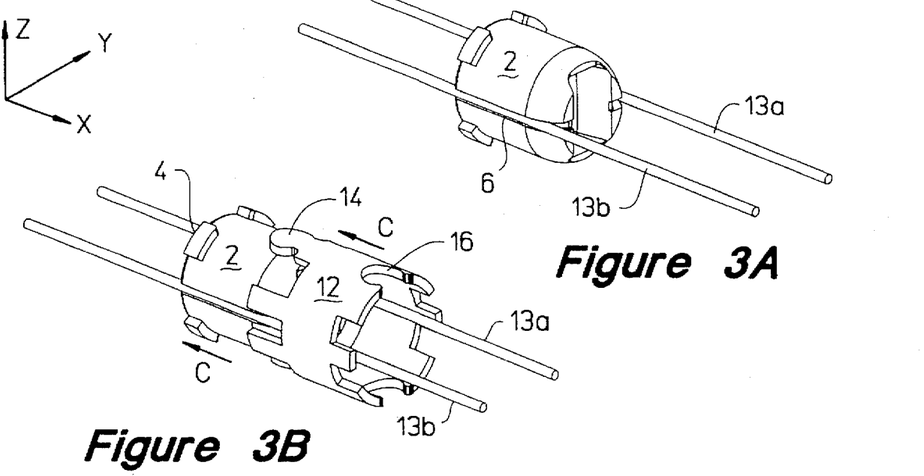
FIGS. 3A–3E show an assembly sequence of the bending neck of the present invention.
Figures 3C, 3D, 3E:
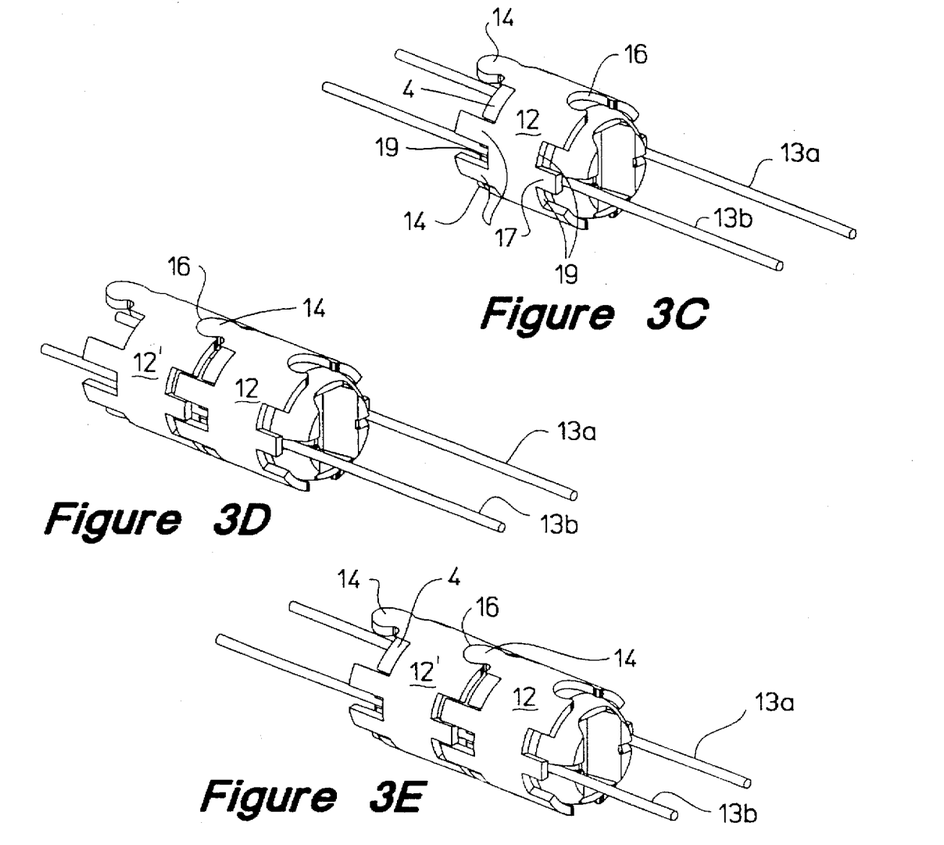

FIGS. 3A–3E show an assembly sequence of a portion of the bending neck of the present invention. A series of cascaded links 2 and sleeves 12 are used in the construction of the bending neck. In FIG. 3A, a cables 13a, 13b are shown inserted in each of the diametrically opposed channels 6 of the link 2. FIGS. 3B–C show the sleeve 12 positioned to slide over the link 2. The sleeve 12 is threaded over the end of the cables 13a and 13b and moved in the direction indicated by the arrows C. Once the sleeve 12 is in place, it is engaged and held in place by the tabs 4. The sleeve 12 captively holds the cables 13a and 13b in the channels 6 of the link 2. The pair of diametrically opposed swivel joints 14 at one end of the sleeve 12 is rotationally offset by 90° relative to the channels 6 and the cables 13a and 13b. At the other end of the sleeve 12, the pair of swivel sockets 16 are adapted to receive a corresponding pair of swivel joints 14.

In FIG. 3D a second sleeve 12' is shown pivotally attached to an adjacent sleeve 12. To install the second sleeve 12', it is first threaded over the end of the cables 13a and 13b and is slid next to the adjacent sleeve 12, oriented with the swivel socket 16 of the second sleeve 12' facing the swivel joint 14 of the first sleeve 12. Initially the second sleeve 12' is offset in the Z-axis direction relative to the first sleeve 12. Once the swivel sockets 16 of the second sleeve 12' are aligned with the swivel joints 16 of the first sleeve 12, the second sleeve 12' is moved in the –Z direction to eliminate the offset, such that the swivel joints 14 are captively held by the swivel sockets 16 and the first sleeve 12 and the second sleeve 12' are in coaxial alignment.

As shown in FIG. 3E, a second link 2' is inserted in the second sleeve 12' and also engaged by tabs 4. Although the second link 2' is not visible in FIGS. 3D and 3E, the ball 5 of the second link 2' is inserted into the socket 3 of the first link 2. As with the first link 2, the second link 2' also has the cables 13 guided through the channels 6 and the cables 13 are captively held within the channels 6 by the sleeves 12. Successive sleeves 12 and links 2 are added in an identical sequence, a sleeve 12 with its swivel socket 16 adjacent to the preceding sleeve's 12 swivel joint 14, followed by the insertion of a corresponding link 2 inside the sleeve 12 with the ball 5 of one link 2 inserted into the socket 3 of the preceding link 2, until the desired number of sleeve 12 and link 2 pairs, or segments, is attained. The number of segments is determined by the length of the bending neck needed in a particular application.

Figure 4A:
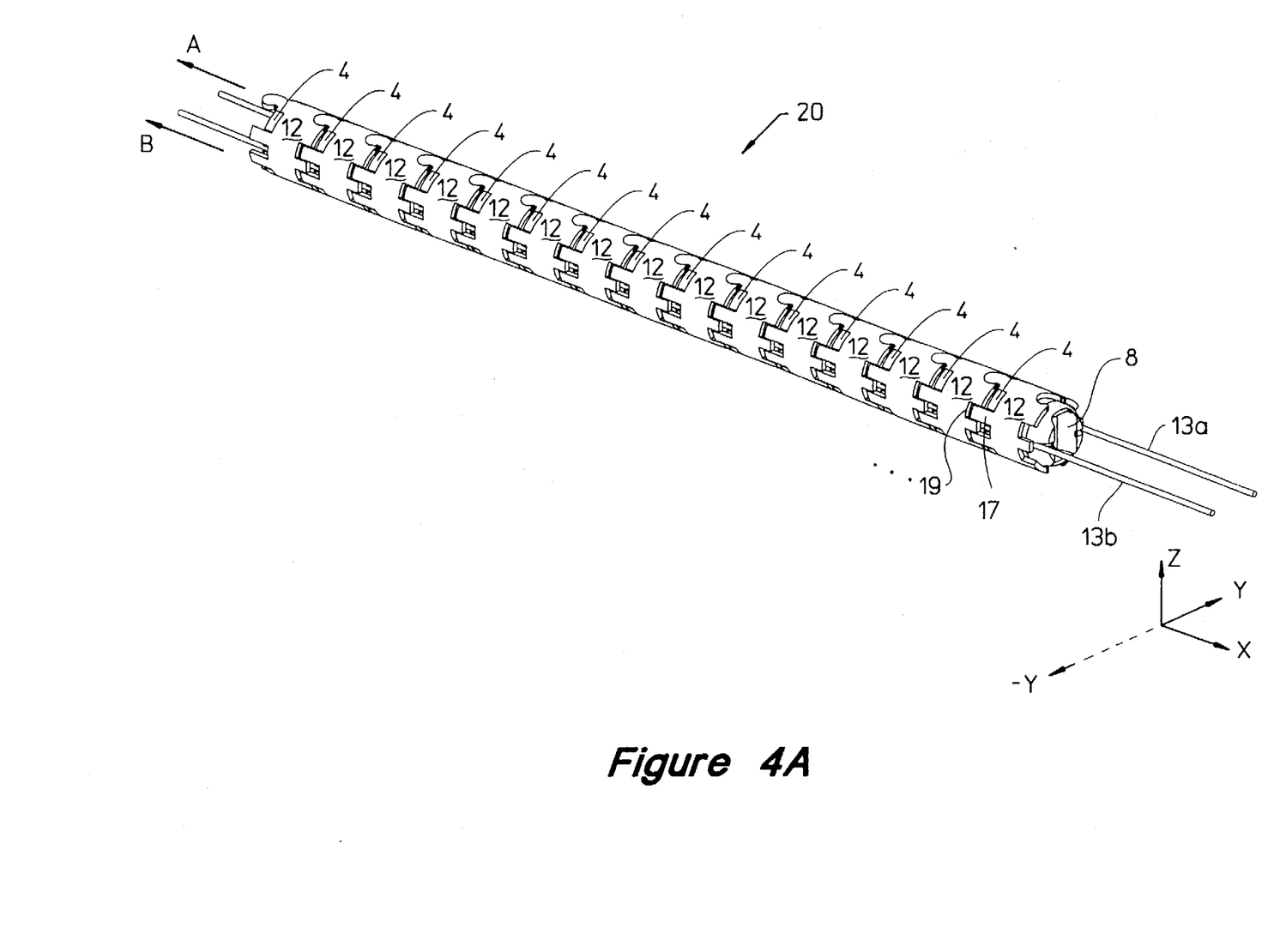
FIG. 4 shows the bending neck formed by multiple link and sleeve pairs of the present invention.

FIG. 4A shows bending neck 20 of the present invention, formed by multiple segments, or link 2 and sleeve 12 pairs.

Figure 4B:
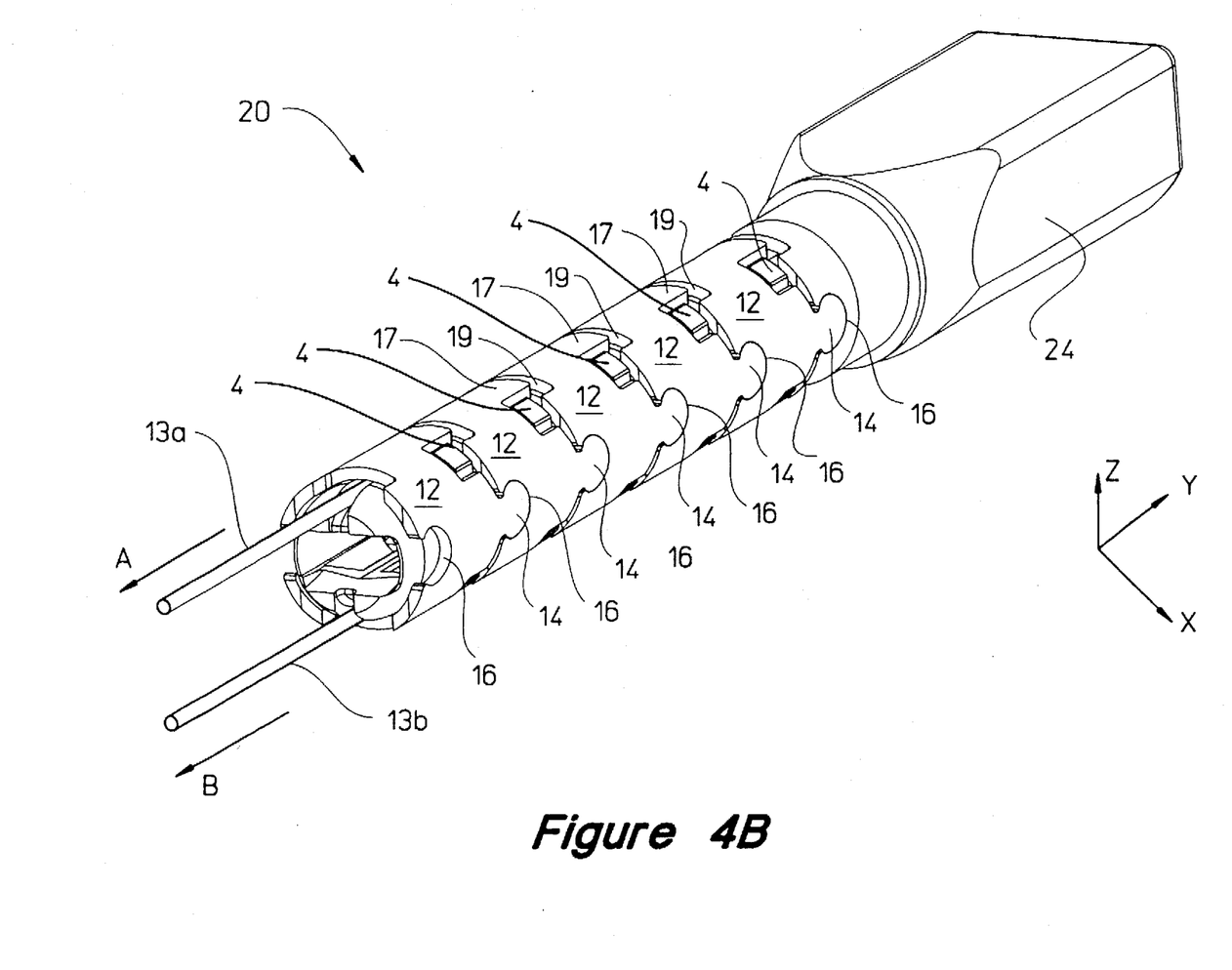

Only the tabs 4 of the links 2 are visible, as the links are internal to the sleeves 12. The number of segments, may vary depending on the length of each link 2 and sleeve 12, and on the overall length of the bending neck 20 desired for a particular application. A head assembly 24, shown in FIG. 4B, is attached to an end of the bending neck 20 and each cable 13a, 13b, is terminated at an anchor point (not shown) at the base of the head assembly. As force is applied to retract either cable 13a or cable 13b, the bending neck 20 articulates in the +Y-axis or the –Y axis direction corresponding to which cable 13a, 13b is being pulled. For example, when cable 13a is pulled in the direction indicated by arrow A, the bending neck 20 curves in the +Y-axis direction. Similarly, when cable 13b is pulled in the direction indicated by arrow B, the bending neck 20 curves in the –Y-axis direction. Motion of the bending neck 20, as the cables 13a and 13b are retracted, is limited to the lateral, or X-Y plane, by the pivotal action of the swivel joints 14 in the swivel sockets 16.

The bending neck 20 may be encased with a continuous elastomeric jacket (not shown) to seal the links 2, the sleeves 12, the cables 13 and other components housed within the bending neck 20 from the patient's body elements. The elastomeric jacket is similar to those used in the art to encase endoscopes, transesophageal ultrasound probes and other invasive medical devices designed for insertion into the body cavities. The smooth surface of the elastomeric jacket provides for easier insertion of the bending neck 20 into the body cavities. The cables 13a and 13b spanning the length of the bending neck 20 are slidably housed in separate confined spaces formed by the channels 6 in the links 2 and covered by the sleeves 12. The channels 6, in which the cables 13 are housed, are distinctly separated from the lumen 8 of each link 2. The cascade of lumens 8 of each end-to-end cascaded link 2 in the bending neck 20, establishes a conduit for any interconnections such as fiber optic cables, drive shafts, electrical conductors and system electronics needed by the particular head assembly 24. When the head assembly 24 is an ultrasound transducer, the conduit contains flexible electronic interconnections that are connected to the ultrasound transducer. The isolation of the lumen 8 and the channels 6 prevents the cables 13a and 13b from rubbing against the interconnection within the conduit formed by the lumens 8, which could damage the interconnections within the conduit and reduce the reliability of the invasive medical device. The bending neck may be attached to an insertion tube (not shown) at the end opposite to the head assembly 24.

Figure 5:
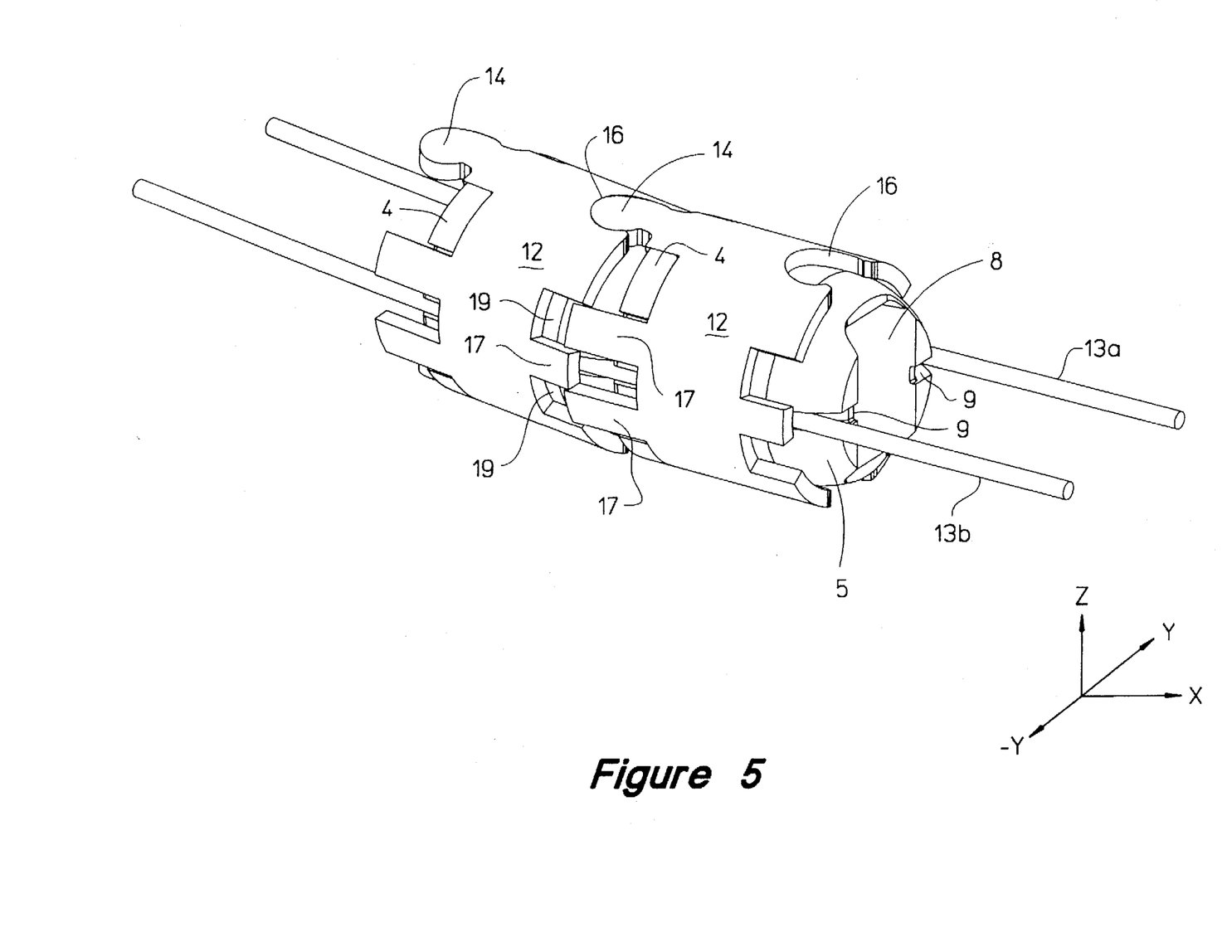
FIG. 5 shows a detailed view of the bending neck of FIG. 4.

FIG. 5 is a detailed view of two segments of the bending neck 20 showing articulation in the X-Y plane. As the bending neck 20 is articulated, one side (in this example, the side proximal to cable 13b) is elongated relative to the other side. On the elongated side, each finger joint 17 partially retreats from its corresponding finger socket 19. On the other, shorter side (in this example, the side proximal to cable 13a) of the articulated bending neck 20 (not visible in FIG. 5), each finger joint 17 further penetrates its corresponding finger socket 19. The finger joints 17 and the finger sockets 19 act as bending stops, limiting the amount of curvature of the bending neck 20 as it is articulated. The length of the finger joints and the depth of the finger sockets define the curvature of the finger joints 17 and finger sockets 19 on each side of the bending neck 20. The finger joints 17 in the finger sockets 19, also prevent the elastomeric jacket from becoming pinched by adjacent sleeves 12 as the bending neck 20 is articulated.

Pivoting of the sleeves 12 in the +Y-axis and the –Y-axis directions is provided by the pivotal action of each swivel joint 14 within its corresponding swivel socket 16. Pivoting of the links 2 inside the sleeves 12 is provided by the pivotal action of the ball 5 in the socket 3 of the adjacent links 2. Rotational spinning of the sleeves 12 about the X-axis, or lengthwise direction, of the bending neck 20 is prevented by engagement of the tabs 4 of the links 2 with the sleeves 12. Rotational spinning of the links 2 and sleeves 12 is avoided to prevent binding of the bending neck 20 as it is articulated. If rotational spinning did occur, it may cause loss of control of the bending neck 20 articulation or it may damage the delicate interconnections within the conduit. Articulation of the dual-axis bending neck 30 may be controlled via a joystick, steering wheel or other device attached to the pull cables 23a, 23b, 23c as shown in FIG. 6.

Figure 6:
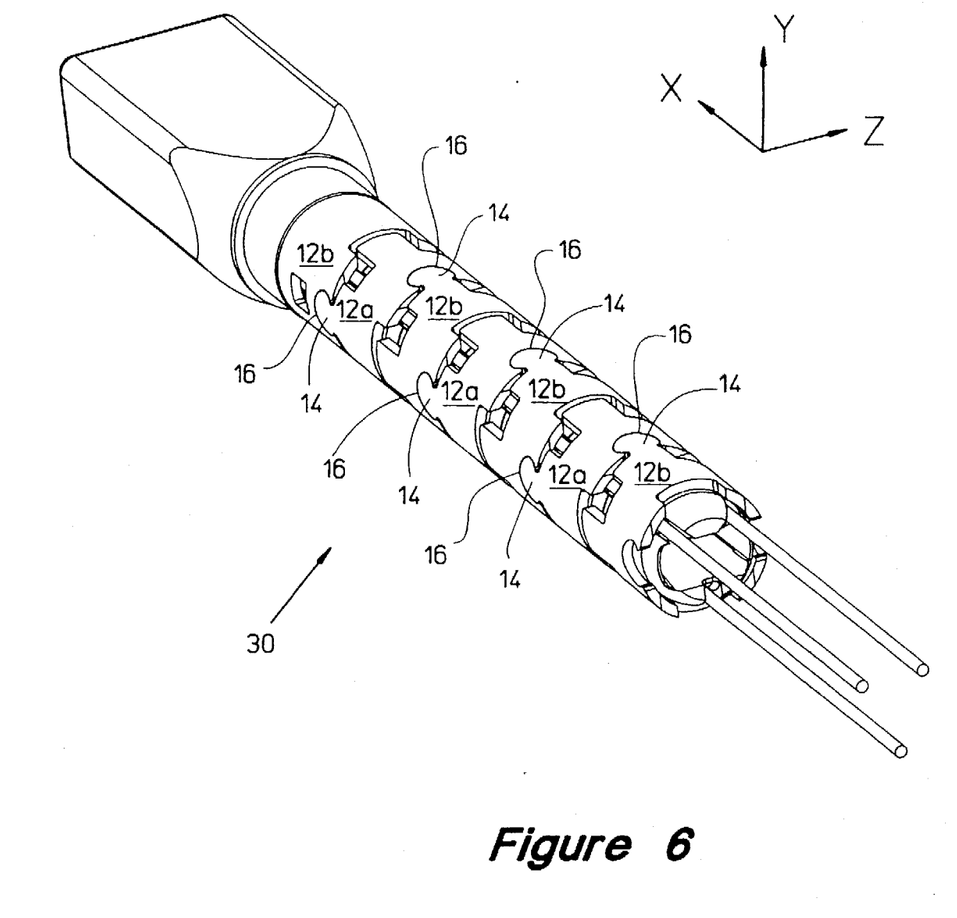
FIG. 6 shows a dual-axis bending neck of an alternate embodiment of the present invention.

FIG. 6 shows a dual-axis bending neck 30 in an alternate embodiment of the present invention. In this alternate embodiment, the swivel joint 14 and corresponding swivel socket 16 of adjacent sleeves 12 alternate in rotational offsets of 90° about the X-axis, or lengthwise axis, of the dual axis bending neck 30. Offset sleeves 12b provide for articulation in the +Y-axis and −Y-axis directions while the on-axis sleeves 12a provide for articulation in the Z-axis and −Z-axis direction. As a result, the dual-axis bending neck 30 may be articulated in any direction within the Y-Z plane.

Figure 7:
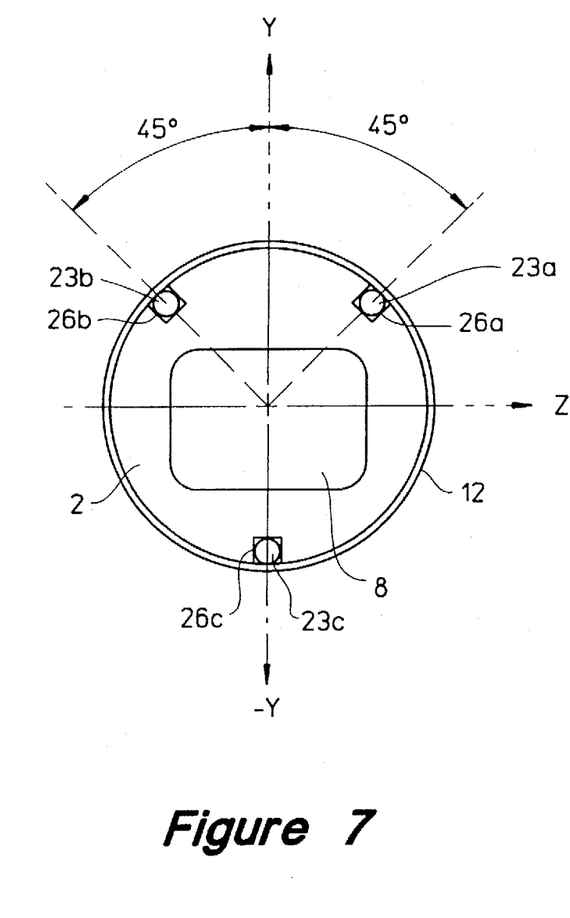
FIG. 7 shows a cross-section of the dual-axis bending neck of FIG. 6.

FIG. 7 shows a cross-sectional view of a the dual-axis bending neck 30, or neck 30. Three channels 26a, 26b, 26c are formed in the link 2 to house corresponding cables 23a, 23b, 23c which are used to articulate the dual-axis bending neck 30. The cables 23a, 23b, 23c are confined to the channels 26a, 26b, 26c by sleeves 12a and 12b. The lumen 8 of each of the cascaded links 2 collectively form a conduit running lengthwise through the dual-axis bending neck 30. The neck 30 has a round cross-section and the channels 26a, 26b are disposed about the center conduit and lie entirely within a first semicircle of the round cross-section. The third channel 26c is disposed about the center conduit and lies entirely within a second semicircle of the round cross-section. The channels 26a, 26b are each symmetrically positioned 45° from the Y-axis. A third channel 26c, is positioned along the −Y-axis. Articulation of the dual-axis bending neck 30, is actuated by pulling one or more of the cables 23a, 23b, 23c. For example, when cable 23c within the channel 26c is pulled, the neck 30 will bend toward the −Y-axis. If cables 23a and 23b are pulled an equal amount, neck 30 will bend toward the +Y-axis. In this embodiment, the neck 30 is articulable in the +Y-axis direction with more force than in the −Y-axis direction due to the angular position of cables 23a and 23b. Articulation in the +Z-axis or −Z-axis directions is accomplished by pulling on either cable 26a or 26b, while allowing the other, un-pulled cable, either 26b or 26a, to slacken.

A greater number of channels may also be formed in the links 2 and the channels may be formed at various rotational positions about the link 2. However, in the second embodiment of the present invention, the rotational positions of the channels 26a, 26b, 26c are chosen so as to provide more bending force as the dual-axis bending neck 30 is articulated in the +Y-axis direction than in the −Y-axis direction. For example, with a force F applied to each of cables 23a and 23b, the achievable bending force of the neck 30 is 2*F*Cos 45°. This bending force is greater than 2*F*Cos 60° as it would be for a force F applied to two cables, were the cables and channels equi-spaced rotationally about the link 2. A high bending force in a particular direction may be useful for applications in which the head assembly 24 attached to the dual-axis bending neck 30 is an ultrasound transducer. For example, ultrasound transducers are pressed firmly against a patient's internal tissues to prevent unwanted reflections during ultrasound imaging. The bending necks of the present invention are not labor intensive to assemble and are useful with a variety of medical devices which require remote articulation and high reliability.

What is claimed:

1. A bending neck for a remotely controlled head assembly used in invasive medical procedures, the bending neck comprising:

a series of cylindrical links having a concave socket at a first end and having a convex ball at the second end, the convex ball of each link in the series adapted for engaging the concave socket of an adjacent link in the series;

a series of tubular sleeves for encircling the links, each sleeve corresponding to a link in the series;

a plurality of channels formed in each link, encased by the tubular sleeve, the channels spanning the length of the links;

a plurality of tabs, at least one tab of the plurality of tabs protruding from each link of the series, engaging the tubular sleeve;

a pair of swivel joints, diametrically opposed, positioned at a first end of each of the sleeves;

a pair of swivel sockets, diametrically opposed, positioned at a second end of each of the sleeves adapted to receive the pair of swivel joints;

a central lumen formed within each of the links, the lumens of the links collectively forming a center conduit, through the length of the bending neck; and a plurality of retractable cables, anchored to the head assembly, each cable threaded through a corresponding channel, and wherein the bending neck is articulated by retraction of at least one the retractable cables.

2. The bending neck of claim 1, each tubular sleeve further comprising at least one pair of slidable finger joints and at least one pair of corresponding finger sockets, the depth of penetration of the slidable finger joints in the corresponding finger sockets determines the maximum articulation of the bending neck.

3. The bending neck of claim 2 wherein the head assembly comprises an ultrasound transducer and wherein the center conduit contains flexible electronic interconnections connected to the ultrasound transducer.

4. A method for assembling a bending neck comprising a series of pivotally hinged segments, each segment comprising an inner link and an outer sleeve, a plurality of channels formed in the inner link and encased by the outer sleeve, the outer sleeve further comprising a pair of swivel joints at one end and a pair of swivel sockets at the other end, the bending neck articulable by a plurality of retractable cables, the method for assembly comprising the steps of:

inserting the plurality of cables in the plurality of channels of a link;

threading a first sleeve over the end of the plurality of cables;

sliding the sleeve over the link;

threading a second sleeve over the end of the plurality of cables such that the pair of swivel joints of the second sleeve is oriented towards the pair of swivel sockets of the first sleeve;

offsetting the second sleeve from the first sleeve in a direction perpendicular to the cables;

aligning the swivel joints of the second sleeve with the swivel sockets of the first sleeve;

engaging the swivel joints with the swivel sockets by eliminating the offset; and inserting a second link in the second sleeve.

\* \* \* \* \*

UNITED STATES PATENT AND TRADEMARK OFFICE
CERTIFICATE OF CORRECTION

PATENT NO. : 5,749,828
DATED : May 12, 1998
INVENTOR(S) : Hubert K. Yeung

It is certified that error appears in the above-identified patent and that said Letters Patent is hereby corrected as shown below:

On the title page, Item[75]:

Delete name of inventor: Rodney J. Solomon

Signed and Sealed this

Fifteenth Day of September, 1998

*Attest:*

BRUCE LEHMAN

*Attesting Officer*   *Commissioner of Patents and Trademarks*